(12) United States Patent
Dahl

(10) Patent No.: US 9,283,182 B2
(45) Date of Patent: Mar. 15, 2016

(54) TOPICAL ANTIVIRAL FORMULATIONS

(75) Inventor: Terrence C. Dahl, Sunnyvale, CA (US)

(73) Assignees: The CONRAD Program of the Eastern Virginia Medical School ("CONRAD"), Arlington, VA (US); International Partnership for Microbicides, Inc., Silver Spring, MD (US)

( * ) Notice: Subject to any disclaimer, the term of this patent is extended or adjusted under 35 U.S.C. 154(b) by 1315 days.

(21) Appl. No.: 12/890,337

(22) Filed: Sep. 24, 2010

(65) Prior Publication Data

US 2011/0120475 A1 May 26, 2011

Related U.S. Application Data

(63) Continuation of application No. 11/174,215, filed on Jul. 1, 2005, now abandoned.

(60) Provisional application No. 60/586,839, filed on Jul. 9, 2004.

(51) Int. Cl.
| | | |
|---|---|---|
| A61F 6/06 | (2006.01) | |
| A61F 6/14 | (2006.01) | |
| A61K 31/675 | (2006.01) | |
| A61K 9/02 | (2006.01) | |
| A61K 9/00 | (2006.01) | |
| A61K 31/505 | (2006.01) | |
| A61F 6/04 | (2006.01) | |

(52) U.S. Cl.
CPC ............... *A61K 9/02* (2013.01); *A61K 9/0014* (2013.01); *A61K 9/0034* (2013.01); *A61K 31/505* (2013.01); *A61K 31/675* (2013.01); *A61F 6/04* (2013.01)

(58) Field of Classification Search
CPC .. A61K 31/675; A61K 9/0036; A61K 9/0034
USPC .................... 424/430, 433; 514/81
See application file for complete search history.

(56) References Cited

U.S. PATENT DOCUMENTS

| | | |
|---|---|---|
| 2,149,240 A | 2/1939 | Crossley et al. |
| 2,330,846 A | 10/1943 | Sander |
| 2,436,184 A | 2/1948 | Stillman et al. |
| 2,467,884 A | 4/1949 | Elias |
| 2,523,841 A | 9/1950 | Taub |
| 2,541,103 A | 2/1951 | Sander et al. |
| 2,623,839 A | 12/1952 | Taub et al. |
| 3,062,715 A | 11/1962 | Reese |
| 3,067,743 A | 12/1962 | Merton et al. |
| 3,108,043 A | 10/1963 | Millman et al. |
| 3,174,900 A | 3/1965 | Wyant et al. |
| 3,244,589 A | 4/1966 | Sunnen |
| 3,640,741 A | 2/1972 | Etes |
| 3,826,828 A | 7/1974 | Morel |
| 3,887,699 A | 6/1975 | Yolles |
| 3,888,975 A | 6/1975 | Ramwell |
| 3,916,898 A | 11/1975 | Robinson |
| 3,989,816 A | 11/1976 | Rajadhyaksha |
| 4,011,312 A | 3/1977 | Reuter et al. |
| 4,017,641 A | 4/1977 | DiGiulio |
| 4,093,730 A | 6/1978 | Butti et al. |
| 4,108,309 A | 8/1978 | Bronner |
| 4,130,667 A | 12/1978 | Smith |
| 4,187,286 A | 2/1980 | Marcus |
| 4,283,325 A | 8/1981 | Berthet et al. |
| 4,306,013 A | 12/1981 | Roach et al. |
| 4,321,277 A | 3/1982 | Saurino |
| 4,360,013 A | 11/1982 | Barrows |
| 4,368,186 A | 1/1983 | Vickery et al. |
| 4,371,518 A | 2/1983 | Gazzani |
| 4,389,330 A | 6/1983 | Tice et al. |
| 4,415,585 A | 11/1983 | Joyce et al. |
| 4,499,154 A | 2/1985 | James et al. |
| 4,537,776 A | 8/1985 | Cooper |
| 4,551,148 A | 11/1985 | Riley, Jr. et al. |
| 4,552,872 A | 11/1985 | Cooper et al. |
| 4,557,934 A | 12/1985 | Cooper |
| 4,589,880 A | 5/1986 | Dunn et al. |
| 4,795,642 A | 1/1989 | Cohen et al. |
| 4,808,176 A | 2/1989 | Kielpikowski |
| 4,816,570 A | 3/1989 | Farquhar |
| 4,895,724 A | 1/1990 | Cardinal et al. |
| 4,954,487 A | 9/1990 | Cooper et al. |
| 4,961,931 A | 10/1990 | Wong |
| 4,968,788 A | 11/1990 | Farquhar |

(Continued)

FOREIGN PATENT DOCUMENTS

| | | |
|---|---|---|
| EP | 1243590 A2 | 9/2002 |
| WO | WO-9119721 A1 | 12/1991 |

(Continued)

OTHER PUBLICATIONS

AID Patient Care and STDs, "Antiviral Briefs," AIDS Patient Care and STDs, 2002, vol. 16, pp. 401.*

Harrison et al. "Topical Microbicides for Disease Prevention: Status and Challenges," Clinical Infectious Diseases, May 2003, vol. 36, No. 10, pp. 1290-1294.*

Ozyazici et al. "In-vitro Evaluation and vaginal absorption of metronidazole suppositories in Rabits," Journal of Drug Targeting, Apr. 2003, vol. 11, No. 3, pp. 177-185.*

Japanese Office Action mailed on Aug. 17, 2011 for corresponding Japanese Patent Application No. 2007-520399 (with English translation), 5 pages.

(Continued)

*Primary Examiner* — Shengjun Wang
(74) *Attorney, Agent, or Firm* — Wilmer Cutler Pickering Hale and Dorr LLP

(57) ABSTRACT

The present invention relates to formulations of nucleotide reverse transcriptase inhibitors (NRTIs), preferably [2-(6-Amino-purin-9-yl)-1-methyl-ethoxymethyl]-phosphonic acid (tenofovir, PMPA), or a physiologically functional derivative thereof, suitable for topical application and their use in the prevention of HIV infections.

1 Claim, No Drawings

(56) References Cited

U.S. PATENT DOCUMENTS

| | | | |
|---|---|---|---|
| 5,015,474 | A | 5/1991 | Parnell |
| 5,143,731 | A | 9/1992 | Viegas et al. |
| 5,185,155 | A | 2/1993 | Behan et al. |
| 5,208,031 | A | 5/1993 | Kelly |
| 5,231,112 | A | 7/1993 | Janoff et al. |
| 5,248,700 | A | 9/1993 | Lance |
| 5,512,289 | A | 4/1996 | Tseng et al. |
| 5,663,159 | A | 9/1997 | Starrett, Jr. et al. |
| 5,733,788 | A | 3/1998 | Bischofberger |
| 5,792,756 | A | 8/1998 | Starrett, Jr. et al. |
| 6,028,115 | A | 2/2000 | Zaneveld et al. |
| 6,057,305 | A | 5/2000 | Holy et al. |
| 6,225,460 | B1 | 5/2001 | Bischofberger et al. |
| 6,274,132 | B1 | 8/2001 | Ratcliff |
| 6,312,662 | B1 | 11/2001 | Erion et al. |
| 2002/0136757 | A1 | 9/2002 | Baron et al. |
| 2003/0180366 | A1 | 9/2003 | Kirschner et al. |
| 2011/0132376 | A1 | 6/2011 | Dahl |

FOREIGN PATENT DOCUMENTS

| | | |
|---|---|---|
| WO | WO-0016755 A2 | 3/2000 |
| WO | WO-03/082193 A2 | 10/2003 |
| WO | WO-03/094920 A1 | 11/2003 |

OTHER PUBLICATIONS

Benzaria et al. "Synthesis, in Vitro Antiviral Evaluation, and Stability Studies of Bis{S-acyl-2-thioethyl) Ester Derviatives . . . " 39:4958-4965; J Med Chem, 1996.

Bundgaard et al. "Design and Application of Prodrugs" pp. 113-191; Textbook of Drug Design and Development, 1991.

Cundy K C et al. "Oral bioavailability of the antiretroviral agent 9-{2-phosphonylmethoxyethyl)adenine (PMEA) from three . . . " 11 (6):839-843; Pharm. Rearch. NY 1994.

De Lombaert et al. "N-Phosphonomethyl dipeptides and Their Phosphonate Prodrugs, a New Generation of Neutral Endopeptidase . . . " 37:498-511; J Med Chem, 1994.

Farquhar et al. "Biologically Reversible Phosphate-Protective Groups" 72(3):324-325; J Pharm Sci, 1983.

Freeman et al. "3 Prodrug Design for Phosphantes and Phosphonates" 34:112-147;Progress in Medicinal Chemistry, 1997.

Hostetler et al."Greatly Enhanced Inhibition of Human Immunodeficiency Virus Type 1 Replication in CEM and HT4-6C Cells by . . . " 36(9):2025-2029; Antimicro AG & Chemo, 1992.

Hostetler et al. "Synthesis and Antiretroviral Activity of Phospholipid Analogs of AZidothymidine . . . " 265(11):6112-6117; J SIOI Chem, 1990.

Jones et al. Minireview: nucleotide prodrugs 27:1-17; Antiviral Res, 1995.

Kararli Tugrul et al "Enhancement oftransdermal transport of azidothymidine{AZT) with novel terpene and terpene-like . . . " 34(1):43-51 Journal of Controlled Release, 1995.

Khamnei et al. "Neighboring Group Catalysis in the Design of Nucleotide Prodrugs." 39:4109-4115; J Med Chem, 1996.

Kucera et al. "Novel Membrane-Interactive Ether Lipid Analogs That Inhibit Infectious HIV-1 Production and Induce Defective Virus . . . " 6:491-501 ;AIDS Res & Hum Retro, 1990.

Mitchell et al. "Bioreversible Protection for the Phospho Group: Bioactivation of the Di(4 acyloxybenzyl) and Mono . . . " 2345-2353; J Chem Soc Perkin Trans I, 1992.

Paquette, Leo A. "Three-Membered Rings with One Hetero Atom" Chptr:1 ; Principals of Modern Heterocyclic Chemistry, 1968.

Paquette, Leo A. "The Four-Membered Heterocycles" Chptr:3; Principals of Modem Heterocyclic Chemistry, 1968.

Paquette, Leo A. "Furan, Pyrrole, and Thiophene" Chptr:4; Principals of Modem Heterocyclic Chemistry, 1968.

Paquette, Leo A. "The Azoles" Chptr:6; Progress in Medicinal Chemistry, 1968.

Paquette, Leo A. "The Pyridine Group" Chptr:?; Principals of Modern Heterocyclic Chemistry, 1968.

Paquette, Leo A. "The Diazines and S-Triazine" Chptr:9; Principals of Modern Heterocyclic Chemistry,1968.

Pauwels Rudi et al. "Development of vaginal microbicides for the prevention of heterosexual . . . " 11 (3):211-221 , Journ. Acquired Imm. Def. Synd. and Human Retro., 1996.

Puech et al "Intracellular delivery of nucleoside monophosphates through a reuctase-mediated activation process." 34:1408-1414; J. Med Chem, 1991.

Siddiqui et al. "Design and Synthesis of Lipophilic Phosphoramidate D4T-MP Prodrugs Expressing High Potency Against HIV in Cell . . . " 42(20):4122-4128; J Med Chem, 1999.

Piantadosi et al. ."Synthesis and Evaluation of Novel Ether Lipd Nucleoside Conjugates for Anti-HIV-1 Activity." 34:1408-1 414; J Med Chem, 1991.

Quast et al. "Herstellung von Methylphosphonsaure-dichlorid"490; Synthesis , 1974.

Turpin A. "Considerations and Development of Topical Microbicides to Inhibit the Sexual . . . " 11(8):1077-1 097; Exp. Op. Investig. Drugs, 2002.

Van Rompay Koen K A et al "Topical administration of low-dose tenofovir disoproxil fumarate to protect infant macaques . . . " 1B6(10); 1508-1513; Joum. Infee. Diseases, 2002.

Tsai et al. "PMPA gel as a topical microbicide for preventing rectal transmission of SHIVA89.6P in macaques," Journal of Medical Primatology, Aug. 2002, vol. 31, No. 4-5, pp. 297-298 Abstract 127.

CDC "HIV/AIDS in the United States, " CDC, 2008, http://www.cdc.gov/hiv/resources/factsheets/pdf/us.pdf.

Korner et al. "Antiretroviral therapy in HIV-infected adults," P&T, 2003, vol. 28, No. 8, pp. 532-544.

PCT/US05/023492 International Search Report (mailed Jun. 22, 2006) (4 pages).

International Search Report and Written Opinion issued by the International Searching Authority for Application No. PCT/US2014/028044 mailed on Jul. 30, 2014 (8 pages).

Investors: Gilead News Release: "Gilead announces initiation of NIH-sponsored phase I trial to evaluate tenofocir topical gel as preventive for vaginal transmission of HIV," May 21, 2002 (4 pgs.).

European Search Report issued by the European Patent Office for Application No. EP 09173070.5 dated Aug. 3, 2011, 6 pages.

\* cited by examiner

TOPICAL ANTIVIRAL FORMULATIONS

FIELD OF THE INVENTION

The invention relates generally to formulations of compounds with antiviral activity and more specifically with anti-HIV properties.

BACKGROUND OF THE INVENTION

Human immunodeficiency virus (HIV) infection and related diseases are a major public health problem worldwide. One approach to the problem of HIV/AIDS is to reduce the risk of transmission of HIV and thus reduce the number of individuals who become newly infected. Even when treatments or cures become available, prevention of infections in the initial instance will likely remain as the first line of defense. For medical, psychological, and economic reasons, it is preferable to prevent the initial infection, rather than treating, individuals with AIDS.

Education in regard to sexually transmitted diseases (STDs), their modes of transmission, and so-called "safe-sex" techniques has shown some promise in reducing the risks of STD transmission through sexual activity. Screening of the blood supply has helped to reduce the risk of transmission of STD-causing organisms via blood transfusions and related medical practices. Even with their known effectiveness in preventing STDs, current safe-sex techniques are not always used, or are not always used properly, for many reasons (e.g. carelessness, lack of knowledge, improper techniques, cultural barriers, unplanned or spontaneous sexual activity, and the like). Moreover, even when used, safe-sex techniques (except perhaps abstinence) are not always effective.

Various commercial vaginal creams and ointments are currently available. Nonoxynol-9, octoxynol-9, and benzalkonium chloride are generally available as suppositories, inserts, creams, films, foams, and gels. Examples of such commercial products include, for example, K-Y Plus™. (2.2 percent nonoxynol-9; Advanced Care Products, Raritan, N.J.); Encare™. (3 percent nonoxynol-9; Thompson Medical Co., West Palm Beach, Fla.); Gynol II (Advanced Care Products, Raritan, N.J.); Ortho Options Conceptrol (Advanced Care Products, Raritan, N.J.); Semicid (Whitehall. Robbins Healthcare, Madison, N.J.); and Advantage-S (Columbia Laboratories, Aventura, Fla.).

However, there is no formulation that is totally effective against HIV. It is desirable, therefore, to provide improved compositions and methods which reduce the risk of HIV transmission and/or infections during sexual activity.

SUMMARY OF THE INVENTION

The present invention relates to formulations of nucleotide reverse transcriptase inhibitors (NRTIs), preferably [2-(6-Amino-purin-9-yl)-1-methyl-ethoxymethyl]-phosphonic acid (tenofovir, PMPA), or a physiologically functional derivative thereof, suitable for topical (e.g. vaginal, rectal, etc.) application and their use in the prevention of HIV infections.

This invention generally relates to compositions and methods which prevent and/or reduce the risk of transmission of HIV through sexual activity. Although it is mainly directed at heterosexual conduct (i.e., male/female vaginal intercourse), the compositions of this invention may also be used by parties engaged in other types of sexual conduct. For example, the compositions of this invention could be used by parties engaged in anal intercourse (male/female or male/male); compositions of this invention intended to be used in anal intercourse are preferably modified to adjust the buffering capacity to pH values normally found in the rectum and by altering the lubricity of the formulation.

For vaginal heterosexual intercourse, the composition may be inserted into the vagina prior to intercourse. For anal intercourse (heterosexual or homosexual), the composition may be inserted into the rectum prior to intercourse. For either vaginal or anal intercourse, the composition may also act as a lubricant. For added protection it is generally preferred that the composition be applied-before intercourse or other sexual activity and that, if appropriate, a condom be used. For even further protection, the composition may be reapplied as soon as possible after completion of the sexual activity.

If desired, flavorants, scents, fragrances, and colorants may be incorporated into the composition so long as they do not interfere with the safety or efficacy of the composition. Indeed, incorporation of such flavorants, scents, fragrances, and colorants into the compositions of this invention may increase the probability that the composition will be used during sexual activity.

One advantage of the present method is that it can be used for protection during a wide variety of sexual activities (vaginal or anal) by heterosexuals, bisexuals, and homosexuals. Another advantage of the present method of reducing the transmission of HIV is that this method may be implemented and/or used most easily by the party being penetrated. Thus, a woman may use the present method to protect herself (as well as her partner) with or without the partner's knowledge of the method being used. Moreover, the partner would not be required to rely on his or her partner's claim of being AIDS-free or agreement to use condoms for protection. Either or both sexual parties (especially the female participant) could initiate and implement the use of the present method. Preferably the method is used before the sexual activity and most preferably both before and after the sexual activity. Moreover, the compositions of this invention offer the added benefit that they are also useful in the prevention and/or treatment of bacterial vaginosis.

DETAILED DESCRIPTION OF EXEMPLARY EMBODIMENTS

Reference will now be made in detail to certain embodiments of the invention, examples of which are illustrated in the accompanying drawings. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims.

DEFINITIONS

Unless stated otherwise, the following terms and phrases as used herein are intended to have the following meanings:

The term "physiologically functional derivative" means a pharmaceutically active compound with equivalent or near equivalent physiological functionality to a given NRTI. As used herein, the term "physiologically functional derivative" includes any: physiologically acceptable salt, ether, ester, prodrug, solvate, stereoisomer including enantiomer, diastereomer or stereoisomerically enriched or racemic mixture, and any other compound which upon administration to the recipient, is capable of providing (directly or indirectly) such a compound or an antivirally active metabolite or residue thereof.

"Bioavailability" is the degree to which the pharmaceutically active agent becomes available to the target tissue after the agent's introduction into the body. Enhancement of the bioavailability of a pharmaceutically active agent can provide a more efficient and effective treatment for patients because, for a given dose, more of the pharmaceutically active agent will be available at the targeted tissue sites.

The compounds of the combinations of the invention may be referred to as "active ingredients" or "pharmaceutically active agents."

The term "prodrug" as used herein refers to any compound that when administered to a biological system generates the drug substance, i.e. active ingredient, as a result of spontaneous chemical reaction(s), enzyme catalyzed chemical reaction(s), and/or metabolic chemical reaction(s).

"Prodrug moiety" means a labile functional group which separates from the active inhibitory compound during metabolism, systemically, inside a cell, by hydrolysis, enzymatic cleavage, or by some other process (Bundgaard, Hans, "Design and Application of Prodrugs" in *Textbook of Drug Design and Development* (1991), P. Krogsgaard-Larsen and H. Bundgaard, Eds. Harwood Academic Publishers, pp. 113-491). Prodrug moieties can serve to enhance solubility, absorption and lipophilicity to optimize drug delivery, bioavailability and efficacy. A "prodrug" is thus a covalently modified analog of a therapeutically-active compound.

"Alkyl" means a saturated or unsaturated, branched, straight-chain, branched, or cyclic hydrocarbon radical derived by the removal of one hydrogen atom from a single carbon atom of a parent alkane, alkene, or alkyne. Typical alkyl groups consist of 1-18 saturated and/or unsaturated carbons, such as normal, secondary, tertiary or cyclic carbon atoms. Examples include, but are not limited to: methyl, Me (—$CH_3$), ethyl, Et (—$CH_2CH_3$), acetylenic (—C≡CH), ethylene, vinyl (—CH=$CH_2$), 1-propyl, n-Pr, n-propyl (—$CH_2CH_2CH_3$), 2-propyl, i-Pr, i-propyl (—CH($CH_3)_2$), allyl (—$CH_2$CH=$CH_2$), propargyl (—$CH_2$C≡CH), cyclopropyl (—$C_3H_5$), 1-butyl, n-Bu, n-butyl (—$CH_2CH_2CH_2CH_3$), 2-methyl-1-propyl, i-butyl (—$CH_2$CH($CH_3)_2$), 2-butyl, s-Bu, s-butyl (—CH($CH_3$)$CH_2CH_3$), 2-methyl-2-propyl, t-Bu, t-butyl (—C($CH_3)_3$), 1-pentyl, n-pentyl, (—$CH_2CH_2CH_2CH_3$), 2-pentyl (—CH($CH_3$)$CH_2CH_2CH_3$), 3-pentyl (—CH($CH_2CH_3)_2$), 2-methyl-2-butyl (—C($CH_3)_2CH_2CH_3$), cyclopentyl (—$C_5H_9$), 3-methyl-2-butyl (—CH($CH_3$)CH($CH_3)_2$), 3-methyl-1-butyl (—$CH_2CH_2$CH($CH_3)_2$), 2-methyl-1-butyl (—$CH_2$CH($CH_3$)$CH_2CH_3$), 1-hexyl (—$CH_2CH_2CH_2CH_2CH_2CH_3$), 5-hexenyl (—$CH_2CH_2CH_2CH_2$CH=$CH_2$) 1-hexyl (—CH($CH_3$)$CH_2CH_2CH_2CH_3$), 3-hexyl (—CH($CH_2CH_3$)($CH_2CH_2CH_3$)), cyclohexyl (—$C_6H_{11}$), 2-methyl-2-pentyl (—C($CH_3)_2CH_2CH_2CH_3$), 3-methyl-2-pentyl (—CH($CH_3$)CH($CH_3$)$CH_2CH_3$), 4-methyl-2-pentyl (—CH($CH_3$)$CH_2$CH($CH_3)_2$), 3-methyl-3-pentyl (—C($CH_3$)($CH_2CH_3)_2$), 2-methyl-3-pentyl (—CH($CH_2CH_3$)CH($CH_3)_2$), 2,3-dimethyl-2-butyl (—C($CH_3)_2$CH($CH_3)_2$), and 3,3-dimethyl-2-butyl (—CH($CH_3$)C($CH_3)_3$.

"Aryl" means a monovalent aromatic hydrocarbon radical of 6-20 carbon atoms derived by the removal of one hydrogen atom from a single carbon atom of a parent aromatic ring system. Typical acyl groups include, but are not limited to, radicals derived from benzene, substituted benzene, naphthalene, anthracene, biphenyl, and the like.

"Arylalkyl:" refers to an acyclic alkyl radical in which one of the hydrogen atoms bonded to a carbon atom, typically a terminal or spa carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group 6 to 20 carbon atoms e.g., the alkyl moiety, including alkanyl, alkenyl or alkynyl groups, of the arylalkyl group is 1 to 6 carbon atoms and the aryl moiety is 5 to 14 carbon atoms.

"Substituted alkyl", "substituted aryl", and "substituted arylalkyl" mean alkyl, aryl, and arylalkyl respectively, in which one or more hydrogen atoms are each independently replaced with a substituent. Typical substituents include, but are not limited to, —X, —R, —O—, —OR, —SR, —S—, —$NR_2$, —$NR_3$, =NR, —$CX_3$, —CN, —OCN, —SCN, —N=C=O, —NCS, —NO, —$NO_2$, =$N_2$, —$N_3$, NC(=O)R, —C(=O)R, —C(=O)NRR—S(=O)$_2$O—, —S(=O)$_2$OH, —S(=O)$_2$R, —OS(=O)$_2$OR, —S(=O)$_2$NR, —S(=O)R, —OP(=O)O$_2$RR, —P(=O)O$_2$RR—P(=O)(O$^-$)$_2$, —P(=O)(OH)$_2$, —C(=O)R, —C(=O)X, —C(S)R, —C(O)OR, —C(O)O$^-$, —C(S)OR, —C(O)SR, —C(S)SR, —C(O)NRR, —C(S)NRR, —C(NR)NRR, where each X is independently a halogen: F, Cl, Br, or I; and each R is independently —H, alkyl, aryl, heterocycle, or prodrug moiety.

"Heteroaryl" and "Heterocycle" refer to a ring system in which one or more ring atoms is a heteroatom, e.g. nitrogen, oxygen, and sulfur (as opposed to carbon). Heterocycles are described in: Katritzky, Alan R., Rees, C. W., and Scriven, E. *Comprehensive Heterocyclic Chemistry* (1996) Pergamon Press; Paquette, Leo A.; *Principles of Modern Heterocyclic Chemistry* W. A. Benjamin, New York, (1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28. Exemplary heterocycles include but are not limited to pyrrole, indole, furan, benzofuran, thiophene, benzothiophene, 2-pyridyl, 3-pyridyl, 4-pyridyl, 2-quinolyl, 3-quinolyl, 4-quinolyl, 2-imidazole, 4-imidazole, 3-pyrazole, 4-pyrazole, pyridazine, pyrimidine, pyrazine, purine, cinnoline, pthalazine, quinazoline, quinoxaline, 3-(1,2,4-N)-triazolyl, 5-(1,2,4-N)-triazolyl, 5-tetrazolyl, 4-(1-O, 3-N)-oxazole, 3-N)-oxazole, 4-(1-S, 3-N)-thiazole, 5-(1-S, 3-N)-thiazole, 2-benzoxazole, 2-benzothiazole, 4-(1,2,3-N)-benzotriazole, and benzimidazole.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and I or (+) and (−) are employed to designate the sign of rotation of plane-polarized light by the compound, with (−) or 1 meaning that the compound is levorotatory. A compound prefixed with (+) or d is dextrorotatory. For a given chemical structure, these compounds, called stereoisomers, are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate. The terms "racemic mixture" and "racemate" refer to an equimolar mixture of two enantiomeric species, devoid of optical activity.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

"Nucleoside and Nucleotide Reverse Transcriptase Inhibitors" or "NRTIs" include those compounds that exhibit anti-HIV effects by inhibiting the activity of HIV reverse transcriptase. Examples include, but are not limited to, abacavir (ABC), didanosine (ddI), emtricitabine (FTC), lamivudine (3TC), stavudine (d4T), tenofovir (TFV), zidovudine (AZT) and zalcitabine (ddC), and their physiologically functional derivatives. One or more NRTIs may be used in a formulation of this invention.

"Topical" formulations include those suitable for nasal, oral, rectal, transdermal, and vaginal administration.

PMPA or tenofovir (U.S. Pat. Nos. 4,808,716, 5,733,788, 6,057,305) has the structure:

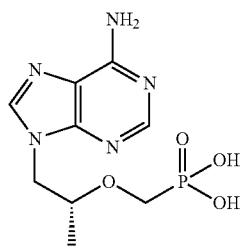 [SMILES: C[C@H](Cn1cnc2c(N)ncnc21)OCP(=O)(O)O]

The chemical names of PMPA, tenofovir include: (R)-9-(2-phosphonylmethoxypropyl)adenine; and phosphonic acid, [[(1R)-2-(6-amino-9H-purin-9-yl)-1-methylethoxy]methyl]. The CAS Registry number is 147127-20-6.

Tenofovir disoproxil fumarate (DF) is a nucleotide reverse transcriptase inhibitor approved in the United States for the treatment of HIV-1 infection in combination with other antiretroviral agents. Tenofovir disoproxil fumarate or Viread® (Gilead Science, Inc.) is the fumarate salt of tenofovir disoproxil. Viread® may be named as: 2,4,6,8-Tetraoxa-5-phosphanonanedioic acid, 5-[[(1R)-2-(6-amino-9H-purin-9-yl)-1-methylethoxy]methyl]-, bis(1-methylethyl)ester, 5-oxide, (2E)-2-butenedioate (1:1). The CAS Registry number is 202138-50-9.

Physiologically functional derivatives of tenofovir include the compounds PMEA and PMPA. PMEA and PMPA have the structures:

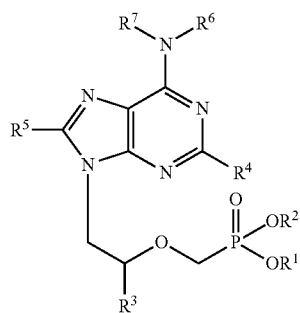

where PMEA ($R^3$ is H) and PMPA ($R^3$ is $C_1$-$C_6$ alkyl, $C_1$-$C_6$ substituted alkyl, or $CH_2OR^8$ where $R^8$ is $C_1$-$C_6$ alkyl, $C_1$-$C_6$ hydroxyalkyl or $C_1$-$C_6$ haloalkyl. $R^6$ and $R^7$ are independently H or $C_1$-$C_6$ alkyl. $R^4$ and $R^5$ are independently H, $NH_2$, NHR or $NR_2$ where R is $C_1$-$C_6$ alkyl. $R^1$ and $R^2$ are independently H, $C_1$-$C_6$ alkyl, $C_1$-$C_6$ substituted alkyl, $C_6$-$C_{20}$ aryl, $C_6$-$C_{20}$ substituted aryl, $C_6$-$C_{20}$ arylalkyl, $C_6$-$C_{20}$ substituted arylalkyl, acyloxymethyl esters —$CH_2OC(=O)R^9$ (e.g. POM) or acyloxymethyl carbonates —$CH_2OC(=O)OR^9$ (e.g. POC) where $R^9$ is $C_1$-$C_6$ alkyl, $C_1$-$C_6$ substituted alkyl, $C_6$-$C_{20}$ aryl or $C_6$-$C_{20}$ substituted aryl. For example, $R^1$ and $R^2$ may be pivaloyloxymethoxy, POM, —$CH_2OC(=O)C(CH_3)_3$ or POC, —$CH_2OC(=O)OC(CH_3)_3$. Also for example, tenofovir has the structure where $R^3$ is $CH_3$, and $R^1$, $R^2$, $R^4$, $R^5$, $R^6$ and $R^7$ are H. Dialkyl phosphonates may be prepared according to the methods of: Quast et. al. (1974) *Synthesis* 490; Stowell et. al. (1990) *Tetrahedron Lett.* 3261; U.S. Pat. No. 5,663,159.

PMPA may be enantiomerically-enriched or purified (single stereoisomer) where the carbon atom bearing $R^3$ may be the R or S enantiomer. PMPA may be a racemate, i.e. a mixture of R and S stereoisomers.

The invention includes all enantiomers, diastereomers, racemates, and enriched stereoisomer mixtures of PMPA, and physiologically functional derivatives thereof.

The invention includes all prodrugs of tenofovir. A large number of structurally-diverse prodrugs have been described for phosphonic acids (Freeman and Ross in *Progress in Medicinal Chemistry* 34: 112-147 (1997). A commonly used prodrug class is the acyloxyalkyl ester, which was first used as a prodrug strategy for carboxylic acids and then applied to phosphates and phosphonates by Farquhar et. al. (1983) *J. Pharm. Sci,* 72: 324; also U.S. Pat. Nos. 4,816,570, 4,968, 788, 5,663,159 and 5,792,756. Subsequently, the acyloxyalkyl ester was used to deliver phosphonic acids across cell membranes and to enhance oral bioavailability. A close variant of the acyloxyalkyl ester strategy, the alkoxycarbonyloxyalkyl ester, may also enhance oral bioavailability as a prodrug moiety in the compounds of the combinations of the invention. Aryl esters of phosphorus groups, especially phenyl esters, are reported to enhance oral bioavailability (DeLambert et. al. (1994) *J. Med. Chem.* 37: 498). Phenyl esters containing a carboxylic ester ortho to the phosphate have also been described (Khamnei and Torrence, (1996) *J. Med. Chem.* 39:4109-4115). Benzyl esters are reported to generate the parent phosphonic acid. In some cases, substituents at the ortho- or para-position may accelerate the hydrolysis. Benzyl analogs with an acylated phenol or an alkylated phenol may generate the phenolic compound through the action of enzymes, e.g. esterases, oxidases, etc., which in turn undergoes cleavage at the benzylic C—O bond to generate the phosphoric acid and the quinone methide intermediate. Examples of this class of prodrugs are described by Mitchell et. al. (1992) *J. Chem. Soc. Perkin Trans. 1* 2345; Brook et. al., WO 91/19721. Still other benzylic prodrugs have been described containing a carboxylic ester-containing group attached to the benzylic methylene (Glazier et. al., WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et. al. (1993) *Antiviral Res.,* 22:155-174; Benzaria et. al. (1996) *J. Med. Chem.* 39: 4958). Cyclic phosphonate esters have also been described as prodrugs of phosphorus-containing compounds.

Prodrug esters in accordance with the invention are independently selected from the following groups: (1) mono-, di-, and tri-phosphate esters of tenofovir or any other compound which upon administration to a human subject is capable of providing (directly or indirectly) said mono-, di, or triphosphate ester; (2) carboxylic acid esters (3) sulphonate esters, such as alkyl- or aralkylsulphonyl (for example, methanesulphonyl); (4) amino acid esters (for example, alanine, L-valyl or L-isoleucyl); (5) phosphonate; and (6) phosphonamidate esters. Ester groups (1)-(6) may be substituted with; straight or branched chain $C_1$-$C_{18}$ alkyl (for example, methyl, n-propyl, t-butyl, or n-butyl); $C_3$-$C_2$ cycloalkyl; alkoxyalkyl (for example, methoxymethyl); arylalkyl (for example, benzyl); aryloxyalkyl (for example, phenoxymethyl); $C_5$-$C_{20}$ aryl (for example, phenyl optionally substituted by, for example, halogen, $C_1$-$C_4$ alkyl, or $C_1$-$C_4$ alkoxy); or amino. An exemplary aryl moiety present in such esters comprises a phenyl or substituted phenyl group. Many phosphate prodrug moieties are described in U.S. Pat. No. 6,312,662; Jones et. al. (1995) *Antiviral Research* 27:1-17; Kucera et. al. (1990) *AIDS Res. Hum. Retro Viruses* 6:491-501; Piantadosi et. al. (1991) *J. Med. Chem.* 34:1408-14; Hosteller et. al. (1992) *Antimicrob. Agents Chemother.* 36:2025-29; Hostetler et. al. (1990) *J. Biol. Chem.* 265:611127; and Siddiqui et. al. (1999) *J. Med. Chem.* 42:4122-28.

Pharmaceutically acceptable prodrugs refer to a compound that is metabolized in the host, for example hydrolyzed or oxidized, by either enzymatic action or by general acid or base solvolysis, to form an active ingredient. Typical examples of prodrugs of the active ingredients of the combinations of the invention have biologically labile protecting groups on a functional moiety of the active compound. Prodrugs include compounds that can be oxidized, reduced, aminated, deaminated, esterified, deesterified, alkylated, dealkylated, acylated, deacylated, phosphorylated, dephosphorylated, or other functional group change or conversion involving forming or breaking chemical bonds on the prodrug.

Any reference to any of the above compounds also includes a reference to a physiologically acceptable salt thereof. Examples of physiologically acceptable salts of tenofovir and is physiologically acceptable derivatives include salts derived from an appropriate base, such as an alkali metal (for example, sodium), an alkaline earth (for example, magnesium), ammonium and $NX_4^+$ (wherein X is $C_1$-$C_4$ alkyl). Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids.

Physiologically acceptable salts of a compound of an hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the invention will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

Formulations include those suitable for nasal, oral, rectal, transdermal, and vaginal administration.

Formulations suitable for topical administration in the mouth include lozenges comprising the active ingredient in a flavored base, usually sucrose and acacia or tragacanth; pastilles comprising the active ingredient in an inert basis such as gelatin and glycerin, or sucrose and acacia; and mouthwashes comprising the active ingredient in a suitable liquid carrier. Formulations for rectal administration may be presented as a suppository with a suitable base comprising, for example, cocoa butter. Formulations suitable for vaginal administration may be presented as tablets, pessaries, tampons, creams, gels, pastes, foams or spray formulations containing in addition to the active ingredient such carriers as are known in the art to be appropriate.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of the active ingredient with the softened or melted carrier(s) followed by chilling and shaping in moulds.

In the context of the present invention, it is to be understood that the term topical application includes application to the body cavities as well as to the skin. Thus, in a preferred embodiment, the NRTI is applied to a body cavity such as the anus, the mouth, or the vagina. In a particularly preferred embodiment, the NRTI is applied to the vagina. Thus, the present method may involve topical application to the vagina to prevent HIV infection as a result of vaginal intercourse. Typically, the topical application is carried out prior to the beginning of vaginal intercourse, suitably 0 to 60 minutes, preferably 0 to 5 minutes, prior to the beginning of vaginal intercourse.

The NRTI may be applied to the vagina in a number of forms including aerosols, foams, jellies, creams, suppositories, tablets, tampons, etc. Compositions suitable for application to the vagina are disclosed in U.S. Pat. Nos. 2,149,240, 2,330,846, 2,436,184, 2,467,884, 2,541,103, 2,623,839, 2,623,841, 3,062,715, 3,067,743, 3,108,043, 3,174,900, 3,244,589, 4,093,730, 4,187,286, 4,283,325, 4,321,277, 4,368,186, 4,371,518, 4,389,330, 4,415,585, and 4,551,148, which are incorporated herein by reference, and the present method may be carried out by applying the NRTI to the vagina in the form of such a composition. The composition containing the NRTI may be applied to the vagina in any conventional manner. Suitable devices for applying the composition to the vagina are disclosed in U.S. Pat. Nos. 3,826,828, 4,108,309, 4,360,013, and 4,589,880, which are incorporated herein by reference.

In another embodiment, the present invention involves topical administration of the NRTI to the anus. The composition administered to the anus is suitably a foam, cream, jelly, etc., such as those described above with regard to vaginal application. In the case of anal application, it may be preferred to use an applicator which distributes the composition substantially evenly throughout the anus. For example, a suitable applicator is a tube 2.5 to 25 cm, preferably 5 to 10 cm, in length having holes distributed regularly along its length.

In another embodiment, the present method may be carried out by applying the NRTI orally. Oral application is suitably carried out by applying a composition which is in the form of a mouthwash or gargle. Oral application is especially preferred to prevent infection during dental procedures. Suitably, the composition is applied just prior to the beginning of the dental procedure and periodically throughout the procedure.

The present invention also provides compositions useful for preventing the spread of HIV infection. As noted above, such compositions may be in the form of foams, creams, jellies, suppositories, tablets, aerosols, gargles, mouthwashes, etc. Particularly preferred are vaginal gels. The concentration of NRTI in the composition is such to achieve an effective local anal, oral or vaginal concentration upon administration of the usual amount of the type of composition being applied. In this regard, it is noted that when the composition is in the form of a suppository (including vaginal suppositories), the suppository will usually be 1 to 5 grams, preferably about 3 grams, and the entire suppository will be applied. A vaginal tablet will suitably be 1 to 5 grams, preferably about 2 grams, and the entire tablet will be applied. When the composition is vaginal cream, suitably 0.1 to 2 grams, preferably about 0.5 grams of the cream will be applied. When the composition is a water-soluble vaginal cream, suitably 0.1 to 2 grams, preferably about 0.6 grams, are applied. When the composition is a vaginal spray-foam, suitably 0.1 to 2 grams, preferably about 0.5 grams, of the spray-foam are applied. When the composition is an anal cream, suitably 0.1 to 2 grams, preferably about 0.5 grams of the cream is applied. When the composition is an anal spray-foam, suitably 0.1 to 2 grams, preferably about 0.5 grams of the spray-foam are applied. When the composition is a mouthwash or gargle, suitably 1 to 10 ml, preferably about 5 ml are applied.

In the case of a mouthwash or gargle, it may be preferred to include in the composition an agent which will mask the taste and/or odor of the NRTI. Such agents include those flavoring agents typically found in mouthwashes and gargles, such as spearmint oil, cinnamon oil, etc.

The present compositions may also be in the form of a time-release composition. In this embodiment, the NRTI is incorporated in a composition which will release the active ingredient at a rate which will result in an effective vaginal or anal concentration of NRTI. Time-release compositions are disclosed in Controlled Release of Pesticides and Pharmaceuticals, D. H. Lew, Ed., Plenum Press, New York, 1981; and U.S. Pat. Nos. 5,185,155; 5,248,700; 4,011,312; 3,887,699; 5,143,731; 3,640,741; 4,895,724; 4,795,642; Bodmeier et al, Journal of Pharmaceutical Sciences, vol. 78 (1989); Amies, Journal of Pathology and Bacteriology, vol. 77 (1959); and Pfister et al, Journal of Controlled Release, vol. 3, pp. 229-233 (1986), all of which are incorporated herein by reference.

The present compositions may also be in the form which releases the NRTI in response to some event such as vaginal or anal intercourse. For example, the composition may contain the NRTI in vesicles or liposomes, which are disrupted by the mechanical action of intercourse. Compositions comprising liposomes are described in U.S. Pat. No. 5,231,112 and Deamer and Uster, "Liposome Preparation: Methods and Mechanisms", in Liposomes, pp. 27-51 (1983); Sessa et al, J. Biol. Chem., vol. 245, pp. 3295-3300 (1970); Journal of Pharmaceutics and Pharmacology, vol. 34, pp. 473-474 (1982); and Topics in Pharmaceutical Sciences, D. D. Breimer and P. Speiser, Eds., Elsevier, N.Y., pp. 345-358 (1985), which are incorporated herein by reference.

It should also be realized that the present compositions may be associated with an article, such as an intrauterine device (IUD), vaginal diaphragm, vaginal sponge, pessary condom, etc. In the case of an IUD or diaphragm, time-release and/or mechanical-release compositions may be preferred, while in the case of condoms, mechanical-release compositions are preferred.

In another embodiment, the present invention provides novel articles, which are useful for the prevention of HIV infection. In particular, the present articles are those which release the NRTI when placed on an appropriate body part or in an appropriate body cavity. Thus, the present invention provides IUDs, vaginal diaphragms, vaginal sponges, pessaries, or condoms which contain or are associated with an NRTI.

Thus, the present article may be an IUD which contains one or more NRTIs. Suitable IUDs are disclosed in U.S. Pat. Nos. 3,888,975 and 4,283,325 which are incorporated herein by reference. The present article may be an intravaginal sponge which comprises and releases, in a time-controlled fashion, the NRTI. Intravaginal sponges are disclosed in U.S. Pat. Nos. 3,916,898 and 4,360,013, which are incorporated herein by reference. The present article may also be a vaginal dispenser, which releases the NRTI. Vaginal dispensers are disclosed in U.S. Pat. No. 4,961,931, which is incorporated herein by reference.

The present article may also be a condom which is coated with an NRTI. In a preferred embodiment, the condom is coated with a lubricant or penetration enhancing agent which comprises an NRTI. Lubricants and penetration enhancing agents are described in U.S. Pat. Nos. 4,537,776; 4,552,872; 4,557,934; 4,130,667, 3,989,816; 4,017,641; 4,954,487; 5,208,031; and 4,499,154, which are incorporated herein by reference.

Examples

The following examples further describe and demonstrate particular embodiments within the scope of the present invention. The examples are given solely for illustration and are not to be construed as limitations as many variations are possible without departing from spirit and scope of the Invention. The following examples are intended for illustration only and are not intended to limit the scope of the invention in any way. "Active ingredient" denotes one or more NRTIs, as defined above, preferably tenofovir or a physiologically functional derivative thereof.

A (Controlled Release Formulation):

This formulation is prepared by wet granulation of the ingredients with purified water, followed by the addition of magnesium stearate and compression. The hypromellose can utilize varying viscosity grades.

|  | mg/tablet |
| --- | --- |
| Active ingredient | 300 |
| Hypromellose | 112 |
| Lactose Monohydrate | 53 |
| Pregelatinized Starch | 28 |
| Magnesium Stearate | 7 |
| Purified Water | q.s. |

Drug release takes place over a period of about 6-8 hours and is complete after 12 hours.

Formulation B (Controlled Release Capsule):

The following controlled release capsule formulation is manufactured by preparing a wet granulation of ingredients a, b, c and e, and then extruding the material using an extruder, followed by spheronization of the extrudate and drying. The dried pellets are then coated with a release-controlling membrane (d) or polymer. The final product is filled into a two-piece, hard gelatin or hydroxypropyl methylcellulose capsule.

|  | mg/capsule |
| --- | --- |
| (a) Active Ingredient | 300 |
| (b) Microcrystalline Cellulose | 125 |
| (c) Lactose Monohydrate | 125 |
| (d) Ethyl Cellulose | 13 |
| (e) Purified Water | q.s. |
| (f) Gelatin capsules |  |

Formulation C (Oral Suspension):

The active ingredients are admixed with the other ingredients and filled as dry powder. Purified water is added and mixed well before use.

| Active Ingredient | 300 mg |
| --- | --- |
| Confectioner's Sugar | 2000 mg |
| Simethicone | 300 mg |
| Methylparaben | 30 mg |
| Propylparaben | 10 mg |
| Flavor, Peach | 500 mg |
| Purified Water q.s. to | 5.00 ml |

Formulation ID (Suppository):

One-fifth of the Witepsol H15 is melted in a steam-jacketed pan at 45° C. maximum. The active ingredients are sifted through a 200 micron sieve and added to the molten base with mixing, using a Silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 micron stainless steel screen and, with continuous stirring, is allowed to cool to 40° C. At a temperature of 38° C. to 40° C., 2.02 g of the mixture is filled into suitable, 2 ml plastic molds. The suppositories are allowed to cool to room temperature.

|  | mg/Suppository |
| --- | --- |
| Active Ingredient | 300 |
| Hard Fat, B.P. (Witepsol H15-Dynamit Nobel) | 1770 |

Formulation E (Vaginal Suppositories)

| Active ingredient | 300 mg |
| --- | --- |
| Hexanetriol | 100 mg |
| Polyethylene glycol 1500 | q.s. |

Formulation F (Vaginal Cream)

| Active ingredient | 300 mg |
| --- | --- |
| Nonionic autoemulsifying base | 4 g |
| Water balance to | 100 g |

Formulation G (Vaginal Spray-Foam)

| Active ingredient | 300 mg |
| --- | --- |
| Polyethylene glycol 6000 | 2 g |
| Nonionic emulsifying agent | 2 g |
| Water | 85 g |
| Freon 12/144 (70:30) | 10 g |

Formulation H (Vaginal Gel)

| Tenofovir | 1.00 (% w/w) |
| --- | --- |
| Hydroxyethylcellulose, NF (Natrasol ® □250H) | 2.50 |
| Propylparaben, NF | 0.02 |
| Methylparaben, NF | 0.18 |
| Edetate Disodium, USP | 0.05 |
| Glycerin, USP | 20.00 |
| Citric Acid, USP | 1.00 |
| Purified Water, USP | 75.25 |
| Total | 100.00 |

Sodium hydroxide and hydrochloric acid are used as 10% w/w solutions to adjust pH to a target of 4.4. The methylparaben and propylparaben are dissolved in heated glycerin. Hydroxyethylcellulose is added and dispersed to form an organic phase. Edetate disodium and citric acid are dissolved in purified water, tenofovir is added and dispersed, pH adjusted to 4.4, and solution clarified by passage through a 0.22 µm filter. Aqueous and organic phases are mixed, stirred well then filled into tubes or applicators.

Safety and Tolerability

Tenofovir vaginal gel used 1% BID was well-tolerated in abstinent and sexually active HIV(−) and HIV(+) women, with limited systemic absorption and with possible beneficial effects on vaginal microflora.

All publications and patent applications cited herein are incorporated by reference to the same extent as if each individual publication or patent application was specifically and individually indicated to be incorporated by reference.

Although certain embodiments have been described in detail above, those having ordinary skill in the art will clearly understand that many modifications are possible in the embodiments without departing from the teachings thereof. All such modifications are intended to be encompassed within the claims of the invention.

The following are claims of the invention:

1. A method for prophylactically reducing a risk of HIV transmission and/or infection during sexual activity between two animals, wherein at least the first animal is infected with HIV, which comprises administering to the second animal an effective amount of a topical formulation comprising an effective amount of a nucleotide reverse transcriptase inhibitor (NRTI) in combination with a pharmaceutically acceptable vehicle, wherein the NRTI further comprises [2-(6-amino-purin-9-yl)-1-methyl-ethoxymethyl]-phosphonic acid (tenofovir) or a physiologically functional derivative thereof, and the topical formulation further comprises a vaginal gel formulation comprising:

| [2-(6-amino-purin-9-yl)-1-methyl-ethoxymethyl]-phosphonic acid | 1.00 (% w/w) |
| --- | --- |
| Hydroxyethylcellulose | 2.50 |
| Propylparaben | 0.02 |
| methylparaben | 0.18 |
| edetate disodium | 0.05 |
| glycerin | 20.00 |

-continued

| | |
|---|---|
| citric acid | 1.00 |
| purified water | 75.25. |

* * * * *